United States Patent
Kim et al.

(10) Patent No.: US 10,591,597 B2
(45) Date of Patent: Mar. 17, 2020

(54) ULTRASOUND IMAGING APPARATUS AND METHOD FOR CONTROLLING THE SAME

(71) Applicant: SAMSUNG ELECTRONICS CO., LTD., Suwon-si (KR)

(72) Inventors: Kyuhong Kim, Seoul (KR); Youngihn Kho, Seoul (KR); Baehyung Kim, Yongin-si (KR); Suhyun Park, Hwaseong-si (KR); Jongkeun Song, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 832 days.

(21) Appl. No.: 14/632,614

(22) Filed: Feb. 26, 2015

(65) Prior Publication Data
US 2015/0293215 A1 Oct. 15, 2015

(30) Foreign Application Priority Data
Apr. 15, 2014 (KR) ........................ 10-2014-0044640

(51) Int. Cl.
*G01S 7/52* (2006.01)
*G01S 15/89* (2006.01)
*A61B 8/00* (2006.01)
*A61B 8/08* (2006.01)

(52) U.S. Cl.
CPC ........ *G01S 15/8993* (2013.01); *A61B 8/4405* (2013.01); *A61B 8/466* (2013.01); *A61B 8/483* (2013.01); *G01S 7/52047* (2013.01)

(58) Field of Classification Search
CPC ........ G01S 7/52; G01S 15/89; G01S 15/8993; G01S 7/52047; G06T 15/08; A61B 8/4405; A61B 8/466; A61B 8/483

USPC ............................................................ 367/7
See application file for complete search history.

(56) References Cited

U.S. PATENT DOCUMENTS

| | | | | |
|---|---|---|---|---|
| 5,388,461 A * | 2/1995 | Rigby | ................ | G01S 7/52023 600/442 |
| 9,700,284 B2 * | 7/2017 | Kapoor | ................... | A61B 8/483 |
| 2002/0193688 A1 * | 12/2002 | Hwang | .............. | G01N 29/0609 600/437 |
| 2005/0049502 A1 * | 3/2005 | Schoisswohl | ........ | A61B 8/0866 600/453 |

(Continued)

FOREIGN PATENT DOCUMENTS

| JP | 2012-223584 A | 11/2012 |
|---|---|---|
| KR | 2002-0044555 A | 6/2002 |

(Continued)

OTHER PUBLICATIONS

Alexander—Resolution in ultrasound imaging (Year: 2011).*

*Primary Examiner* — Hovhannes Baghdasaryan
*Assistant Examiner* — Amie M Ndure
(74) *Attorney, Agent, or Firm* — Sughrue Mion, PLLC

(57) ABSTRACT

An ultrasound imaging apparatus includes an ultrasonic probe configured to transmit an ultrasound to an object, receive an echo signal reflected from the object, and output the echo signal; a quality determiner configured to receive the echo signals and determine quality of voxels of a three-dimensional (3D) volume of the object to be rendered based on observation information of the 3D volume; and a beamformer configured to perform beamforming on the echo signal based on the quality of the voxels to generate an output signal.

16 Claims, 17 Drawing Sheets

(56) References Cited

U.S. PATENT DOCUMENTS

| | | | |
|---|---|---|---|
| 2005/0049503 A1* | 3/2005 | Schoisswohl | A61B 8/0866 600/453 |
| 2005/0113695 A1* | 5/2005 | Miller | A61B 8/00 600/443 |
| 2005/0114175 A1* | 5/2005 | O'Dea | A61B 8/00 705/2 |
| 2005/0273009 A1* | 12/2005 | Deischinger | A61B 8/00 600/437 |
| 2009/0112095 A1* | 4/2009 | Daigle | A61B 8/06 600/454 |
| 2009/0299184 A1* | 12/2009 | Walker | G01S 7/52046 600/447 |
| 2011/0091086 A1* | 4/2011 | Seko | A61B 8/463 382/131 |
| 2011/0137168 A1* | 6/2011 | Lee | G01S 7/52063 600/443 |
| 2011/0144495 A1* | 6/2011 | Wilkening | A61B 8/0883 600/443 |
| 2011/0306886 A1* | 12/2011 | Daft | A61B 8/0825 600/459 |
| 2012/0212618 A1* | 8/2012 | Park | G01S 15/8977 348/163 |
| 2013/0131514 A1 | 5/2013 | Kim et al. | |
| 2014/0058266 A1* | 2/2014 | Call | A61B 8/14 600/448 |
| 2014/0269209 A1* | 9/2014 | Smith | A61B 8/4461 367/140 |
| 2015/0133784 A1* | 5/2015 | Kapoor | A61B 8/483 600/438 |
| 2016/0262720 A1* | 9/2016 | Henderson | A61B 8/466 |

FOREIGN PATENT DOCUMENTS

| | | |
|---|---|---|
| KR | 10-2012-0095730 A | 8/2012 |
| KR | 10-2012-0119787 A | 10/2012 |
| KR | 10-2013-0054743 A | 5/2013 |

* cited by examiner

FIG. 7

```
for i=1:xSize
    for j=1:ySize
        for k=1:zSize
            length = sqrt((i-vp1(X))^2+(j-vp1(Y))^2+(k-vp1(Z))^2);
            if length < thr1
                vol(i,j,k) = 5;
            elseif length < thr2
                vol(i,j,k) = 4;
            elseif length < thr3
                vol(i,j,k) = 3;
            elseif length < thr4
                vol(i,j,k) = 2;
            else
                vol(i,j,k) = 1;
            end
        end
    end
end
```

ULTRASOUND IMAGING APPARATUS AND METHOD FOR CONTROLLING THE SAME

CROSS-REFERENCE TO RELATED APPLICATION

This application claims priority from Korean Patent Application No. 10-2014-0044640, filed on Apr. 15, 2014, in the Korean Intellectual Property Office, the entire disclosure of which is incorporated herein by reference in its entirety.

BACKGROUND

1. Field

Apparatuses and methods consistent with exemplary embodiments relate to an ultrasound imaging apparatus and a method for controlling the same, in which beamforming is performed based on qualities of voxels of a three-dimensional (3D) volume.

2. Description of the Related Art

An ultrasound imaging apparatus transmits ultrasound signals toward a target part within an object, collects echo signals reflected from the target part, and generates an ultrasonic image. To this end, the ultrasound imaging apparatus performs beamforming to estimate amplitude of a reflected wave in a particular space from a plurality of channel data collected by an ultrasonic probe from the echo signals.

Beamforming is an operation to focus echo signals input through multiple ultrasonic sensors, e.g., transducers, by compensating time difference of the echo signals and stressing or attenuating a signal on a particular position using a predetermined weight, i.e., a beamforming coefficient for each echo signal. After performing beamforming, the ultrasound imaging apparatus may generate an ultrasonic image representing an internal structure of the object and display the ultrasonic image.

Depending on characteristics of the beamforming coefficient used in beamforming, beamforming may be data-independent beamforming or adaptive. The data-independent beamforming uses a set weight regardless of the input echo signal while the adaptive beamforming determines a weight based on the input echo signal. Accordingly, the weight in the adaptive beamforming varies with input echo signals.

SUMMARY

One or more exemplary embodiments provide an ultrasound imaging apparatus and a method for controlling the same, in which a quality of each voxel of a three-dimensional (3D) volume is determined and beamforming is performed based on the determined quality.

In accordance with an aspect of an exemplary embodiment, an ultrasound imaging apparatus is provided. The ultrasound imaging apparatus includes an ultrasonic probe for irradiating an ultrasound to an object, receiving an echo signal reflected from the object, and outputting the echo signal; a quality determiner for determining a quality of each voxel of a three-dimensional (3D) volume based on observation information; and a beamformer for performing beamforming differently based on the quality to generate an output signal.

The quality determiner may include an observation information detector for extracting an observation center and observation direction from the 3D volume.

The quality determiner may include a quality calculator for calculating a distance between each voxel and the observation center based on the observation information; and calculating a quality of the voxel based on the distance.

The quality determiner may include a quality map storage for storing a quality map that has information about a quality of each voxel of the 3D volume based on the observation information; and a quality retriever for retrieving a quality map that corresponds to the observation information from the quality map storage to determine the quality.

The beamformer may perform beamforming with higher quality as the quality of the voxel determined by the quality determiner is higher, or may perform beamforming to have a higher resolution as the quality determined by the quality determiner is higher.

The beamformer may include a transformer for generating a transformed signal from the echo signal by means of a transformation matrix formed based on a quality determined by the quality determiner; a weight calculator for calculating a signal weight to be applied to the transformed signal; and a combiner for generating the output signal by means of the transformed signal generated by the transformer and the signal weight calculated by the weight calculator.

The transformation matrix may reduce a dimension of the echo signal according to a quality determined by the quality determiner.

The beamformer may include a storage for storing the plurality of basis vectors that form the transformation matrix, and the number of the basis vectors may be determined based on a quality determined by the quality determiner.

The transformation matrix may be formed of a combination of basis vectors obtained through principal component analysis on a quality determined by the quality determiner.

The ultrasound imaging apparatus may further include an image processor for building up a 3D volume based on one or more output signals from the beamformer and rendering the 3D volume into a two dimensional (2D) plane.

In accordance with an aspect of an exemplary embodiment, a method for controlling an ultrasound imaging apparatus is provided. The method includes retrieving observation information from a three dimensional (3D) volume; determining a quality of each voxel of the 3D volume based on the observation information; and performing beamforming differently on voxels based on the quality.

The observation information may include an observation center and observation direction for the 3D volume.

Determining a quality of each voxel may include determining a quality of each voxel based on a distance between the observation center and the voxel of the 3D volume.

Determining a quality of each voxel may include retrieving a quality map having information about a quality of each voxel of the 3D volume based on the observation information; and determining the quality of the voxel according to the retrieved quality map.

Performing beamforming may include performing beamforming such that the higher the quality is, the higher a resolution of the voxel is.

Performing beamforming may include transforming an echo signal to a transformed signal by means of a transformation matrix formed based on the determined quality of each voxel; calculating a signal weight to be applied to the transformed signal; and generating an output signal using the transformed signal and the signal weight.

The transformation vector may be formed of one or more basis vectors generated through principal component analysis, and the number of the basis vectors may be determined based on the determined quality of each voxel.

The method may further include building up a 3D volume based on one or more output signals resulting from beamforming; and rendering the 3D volume image into a two dimensional plane. Other aspects, advantages, and salient features of the disclosure will become apparent to those skilled in the art from the following detailed description, which, taken in conjunction with the annexed drawings, discloses exemplary embodiments of the disclosure

BRIEF DESCRIPTION OF THE DRAWINGS

The above and/or other aspects will become more apparent by describing certain exemplary embodiments with reference to the accompanying drawings, in which:

FIG. 7 shows an example of a function to calculate a quality of a voxel according to an exemplary embodiment;

DETAILED DESCRIPTION

Figure 1:
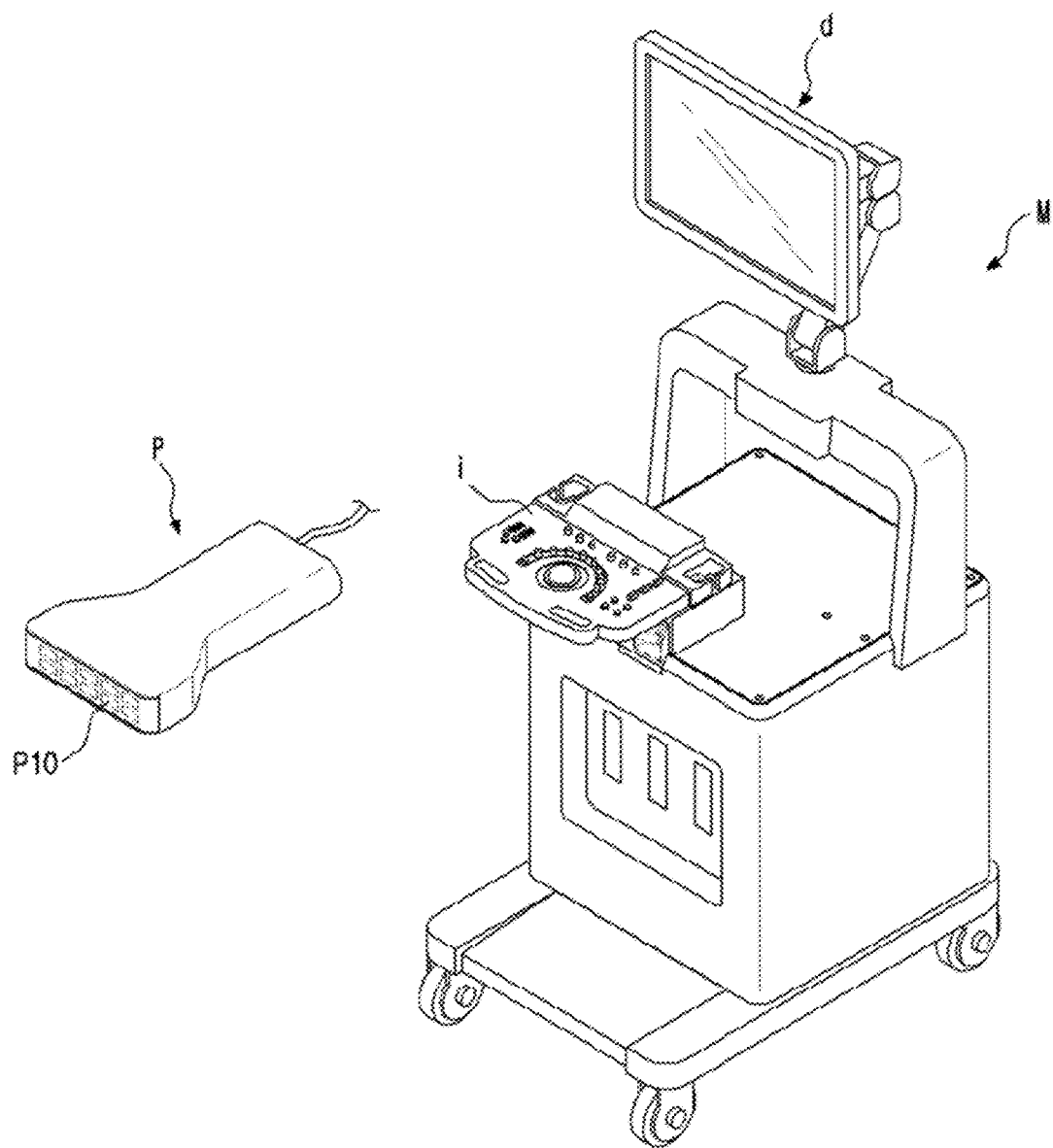
FIG. 1 is a perspective view of an ultrasound imaging apparatus, according to an exemplary embodiment.

Certain exemplary embodiments are described in greater detail below with reference to the accompanying drawings. The disclosure may, however, be embodied in many different forms and should not be construed as being limited to the exemplary embodiments set forth herein; rather, these exemplary embodiments are provided so that this disclosure will be thorough and complete, and will fully convey the concept of the disclosure to those skilled in the art Like reference numerals in the drawings denote like elements, and thus repetitive description will be omitted. In the description, if it is determined that a detailed description of commonly-used technologies or structures related to the exemplary embodiments may unnecessarily obscure the subject matter of the invention, the detailed description will be omitted. It will be understood that, although the terms "first", "second", "third", etc., may be used herein to describe various elements, components, regions, layers and/or sections, these elements, components, regions, layers and/or sections should not be limited by these terms. These terms are only used to distinguish one element, component, region, layer or section from another region, layer or section.

FIG. 1 is a perspective view of an ultrasound imaging apparatus, according to an exemplary embodiment.

The ultrasound imaging apparatus may provide an ultrasonic image of a three-dimensional (3D) volume probed by an ultrasonic probe. The ultrasound imaging apparatus may create the ultrasonic image by controlling each voxel of the 3D volume to have a different quality.

The 3D volume includes elements called 'voxels'. A voxel defines a point in a 3D space given the fact that a pixel defines a point in a two-dimensional (2D) plane. In other words, as compared with the pixel represented by x and y coordinates, the voxel may be represented by x, y, and z coordinates.

More specifically, the ultrasound imaging apparatus may perform beamforming on voxels closer to a viewing (or observation) point of a user with a relatively high quality and on voxels distanced away from the viewing point with a relatively low quality. As such, beamforming may be improved by differently performing the beamforming according to a distance from the viewing point of the user.

Referring to FIG. 1, the ultrasound imaging apparatus may include an ultrasonic probe P and a main unit M. The ultrasonic probe P is configured to transmit ultrasounds to an object, receive echo signals from the object, and output the echo signals to the main unit M. The main unit M is configured to generate an ultrasonic image based on the echo signals received from the ultrasonic probe P.

For convenience of explanation, it will be described herein that the ultrasonic probe P receives and outputs echo signals and the main unit M creates an ultrasonic image. However, exemplary embodiments are not limited thereto. For example, according to an exemplary embodiment, the ultrasonic probe P may perform beamforming. However, in the following description of the ultrasound imaging apparatus, it is assumed that the ultrasonic probe P outputs echo signals and the main unit M performs beamforming or image processing.

As shown in FIG. 1, the main unit M may be a workstation, coupled with the ultrasonic probe P, and include an input unit i and a display d. However, exemplary embodiments are not limited thereto. For convenience of explanation, it is assumed that the main unit M includes the input unit i and the display d.

The input unit i receives predetermined instructions or commands from the user for controlling the ultrasound imaging apparatus. For example, the input unit i may receive a command to change an observation point on a rendered screen or a command to change an observation direction from the user.

The input unit i may also include a user interface such as, e.g., a keyboard, a mouse, a trackball, a touch screen, a paddle, etc., but is not limited thereto.

The display d may display an ultrasonic image obtained in the process of an ultrasonic diagnosis on the screen. For example, the display d may display a 3D volume on a 2D rendered screen.

The display d may include a cathode ray tubes (CRT), a liquid crystal display (LCD), an organic light emitting diode (OLED), etc., but is not limited thereto.

The components of the ultrasound imaging apparatus will be described in detail in connection with FIGS. 2 to 15.

Figure 2:
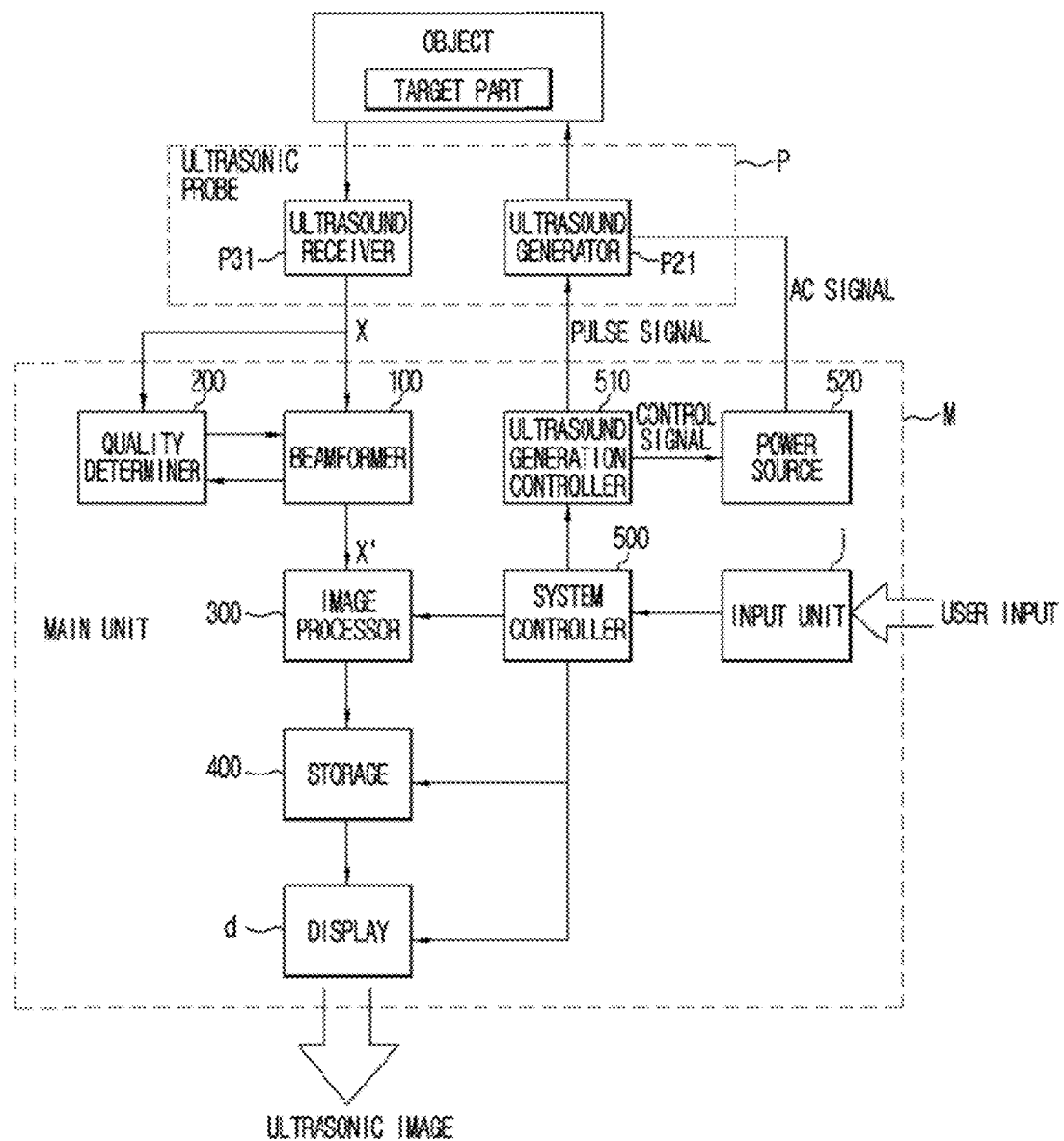
FIG. 2 is a block diagram of an ultrasound imaging apparatus, according to an exemplary embodiment.

FIG. 2 is a block diagram of an ultrasound imaging apparatus, according to an exemplary embodiment.

Figure 3:
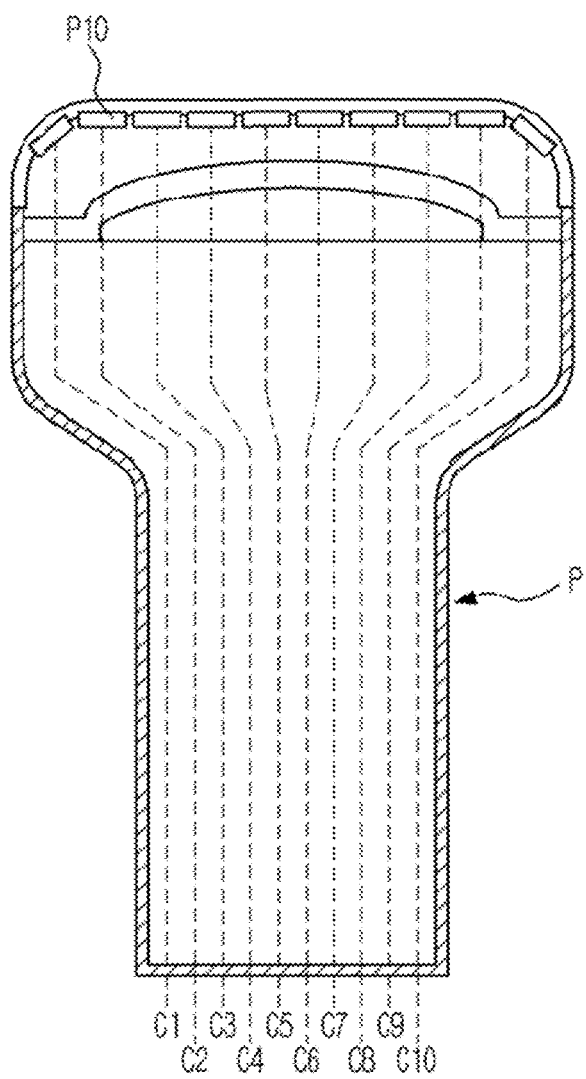
FIG. 3 is a plan view of an ultrasonic probe, according to an exemplary embodiment.

FIG. 3 is a plan view of an ultrasonic probe, according to an exemplary embodiment.

Referring to FIGS. 2 and 3, an ultrasound imaging apparatus includes an ultrasonic probe P.

Referring to FIG. 2, the ultrasonic probe P collects information regarding a target part of an object using ultrasounds. The ultrasonic probe P may be configured to probe a 3D volume.

In an exemplary embodiment, as shown in FIG. 1, the ultrasonic probe P may include a plurality of transducers P10 arranged in a form of a matrix. The transducers P10 may output a plurality of echo signals and create a 3D volume by accumulating the output echo signals.

In another exemplary embodiment, the ultrasonic probe P may include transducers P10 arranged in a row and a mechanism to move the transducers P10. More specifically, rails (not shown) may be arranged on an end portion of the row of the transducers P10 in a direction substantially perpendicular to the direction in which the transducers P10 are arranged. The plurality of echo signals may be obtained by moving the row of the transducers P10 along the rails in a scanning direction, and a 3D volume may be created by accumulating the echo signals.

For convenience of explanation, it is assumed herein that the transducers P10 are arranged in a form of a matrix in the ultrasonic probe P.

Referring to FIG. 3, a plurality of ultrasonic transducers P10 may be installed at one end of the ultrasonic probe P. The ultrasonic transducers P10 generate ultrasounds corresponding to an applied signal or power, transmit the ultrasounds onto an object, receive echo ultrasounds reflected from the object, and generate echo signals for output.

Specifically, the ultrasonic transducers P10 are supplied with power from an external power supply or an internal electricity storage device, e.g., a battery, and generate ultrasounds by using a piezo-electric resonator or a thin film that vibrates according to the applied power. The ultrasonic transducers P10 convert the ultrasounds to echo signals X by generating an alternating current (AC) corresponding to a vibration frequency from the vibration of the piezo-electric resonator or the thin film upon reception of the ultrasound. The ultrasonic transducers P10 may send the echo signals X to the main unit M through a plurality of channels C1, C2, C3, C4, C5, C6, C7, C8, C9, and C10, as shown in FIG. 3.

The ultrasonic transducers P10 may include, e.g., magnetostrictive ultrasonic transducers that use a magnetostrictive effect of a magnetic substance, piezoelectric ultrasonic transducers that use a piezoelectric effect of a piezoelectric substance, or capacitive micromachined ultrasonic transducers (cMUTs) that transmit and receive ultrasounds through vibration of hundreds or thousands of thin films. In addition, different types of transducers that may generate ultrasounds from electrical signals or generate electrical signals from ultrasounds may also be used as the ultrasonic transducers P10.

Figure 4:
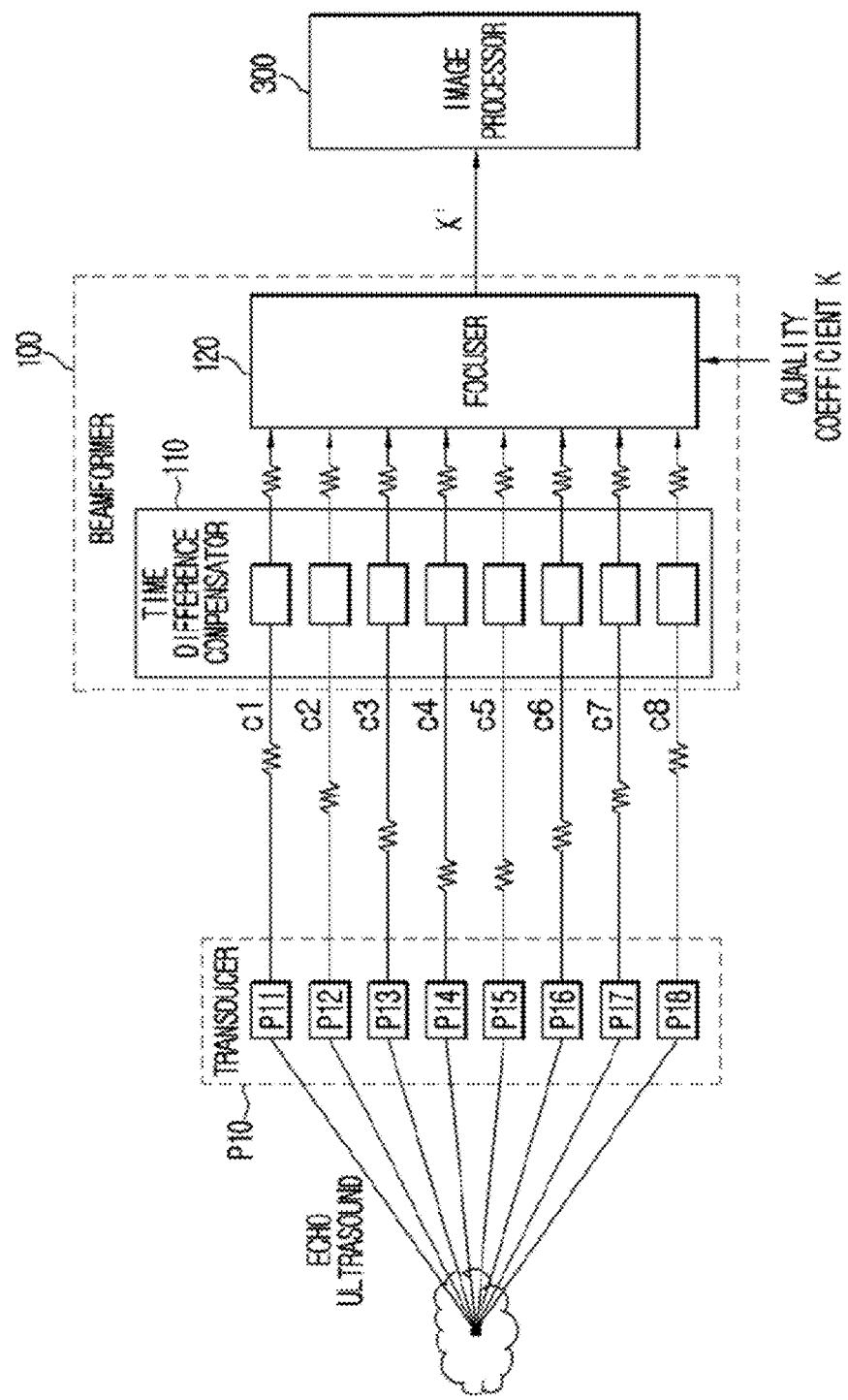
FIG. 4 is a block diagram of a beamformer according to an exemplary embodiment.

FIG. 4 is a block diagram of a beamformer according to an exemplary embodiment.

Referring to FIG. 4, a beamformer 100 receives echo signals X from an ultrasound receiver P31 of the ultrasonic probe P, as shown in FIG. 2, and performs beamforming on the echo signals X to generate an output signal X'. In this regard, beamforming focuses multiple echo signals reflected from a target part to generate a single output signal.

More specifically, beamforming refers to an operation of focusing signals of multiple channels, e.g., channels c1, c2, c3, c4, c5, c6, c7, and c8 in FIG. 4, by compensating time differences among input echo signals of the respective channels upon reception of the multiple echo signals, and stressing or attenuating a signal of a particular channel with a predetermined weight for each echo signal with a time difference compensated.

An ultrasonic image is generated based on the output signal resulting from the beamforming. Thus, beamforming may determine a resolution of an ultrasonic image. However, time delay and power loss may occur to obtain a higher resolution of the ultrasonic image due to a relatively great amount of calculation. In an exemplary embodiment, an ultrasound imaging apparatus differently determines a quality of each voxel of a 3D volume and performs beamforming based on the determined quality. The beamformer 100 according to an exemplary embodiment will be described in detail with reference to FIGS. 2 and 4.

Referring to FIG. 4, the beamformer 100 may include a time difference compensator 110 and a focuser 120. Beamforming may be expressed in the following equation 1:

$$z[n] = \sum_{m=0}^{M-1} w_m[n] x_m[n - \Delta_m[n]] \quad (1)$$

where n represents a position of a target part, and $w_m$ represents a beamforming coefficient applied to an echo signal of an m-th channel at the position n of the target part. $\Delta_m$ represents a value of time delay in transmission of an echo signal input from a particular channel.

The time difference compensator 110 compensates a time difference between echo signals. For example, as shown in FIG. 4, the time difference compensator 110 delays transmission of an echo signal input from a particular channel by a certain time such that echo signals X input from respective channels are sent to the focuser 120 substantially at the same time.

More specifically, the beamformer 100 receives echo signals reflected from the target part. Even though echo ultrasounds are reflected from the same target part, respective ultrasonic transducers P10 installed in the ultrasonic probe P may receive the echo ultrasounds at different points in time.

That is, certain time differences may exist in reception of echo ultrasounds reflected from the same target part. It is because distances between the target part and respective ultrasonic transducers P11, P12, P13, P14, P15, P16, P17, and P18 may be different from each other.

Thus, even if the respective ultrasonic transducers P11 to P18 receive echo ultrasounds at different points in time, the echo ultrasounds may have been reflected from the same target part. Accordingly, the time differences among the echo signals generated by the respective ultrasonic transducers P11 to P18 need to be compensated.

That is, the time difference compensator 110 outputs a signal for each channel with a time difference $\Delta_m$ compensated.

The focuser 120 focuses the signals with time differences compensated according to a quality determined by a quality determiner 200. Quality determined by the quality determiner 200 may be different for each voxel of a 3D volume.

The focuser 120 focuses echo signals by applying a predetermined weight, i.e., a beamforming coefficient w for each input echo signal to stress or attenuate a signal of a particular position. Accordingly, an ultrasonic image may be created according to a user demand or user convenience.

With the time difference compensated, beamforming may be expressed as in the following equation 2:

$$x' = w^H x \quad (2)$$

The echo signals x are signals with time differences compensated by the time difference compensator 110, and the focuser 120 applies weights to the echo signals x to generate an output signal x'.

The focuser 120 may use a different beamforming coefficient w depending on a quality of a voxel determined by the quality determiner 200. More specifically, the focuser 120 may beamform a voxel determined to have a higher quality to have a higher resolution by controlling a weight to be applied thereto, and may beamform a voxel determined to have a lower quality to have a lower resolution by controlling a weight to be applied thereto. In this way, less calculation is needed for beamforming.

For example, the focuser 120 applies a weight to a voxel determined to have a higher quality with a relatively high dimensional beamforming coefficient w and applies a weight to a voxel determined to have a lower quality with a relatively low dimensional beamforming coefficient w.

Furthermore, the focuser 120 may perform adaptive beamforming on a voxel determined to have a higher quality and perform fixed beamforming on a voxel determined to have a lower quality. Fixed beamforming refers to beamforming by applying a predetermined same weight to each input echo signal, and the adaptive beamforming refers to perform beamforming by applying a different weight to each input echo signal.

However, quality-based weight application is not limited thereto and any other weight application may be used as long as a voxel of a higher quality is controlled to have a higher resolution and a voxel of a lower quality is controlled to have a lower resolution. For example, a voxel of a higher quality may be controlled to a higher resolution with greater burden of calculations and a voxel of a lower quality may be controlled to a lower resolution with less burden of calculations. A specific beamforming method will be described later in detail.

The quality determiner 200 may determine qualities of voxels constituting a 3D volume based on observation information. More specifically, the quality determiner 200 may determine a voxel adjacent to an observation center to have a higher quality and a voxel further away from the observation center to have a lower quality. The beamformer 100 performs beamforming according to the determined qualities, thereby increasing calculation performance.

The quality determiner 200 may provide a determined quality coefficient K of each voxel to the beamformer 100. The quality coefficient K includes quality information for each voxel. For example, the quality coefficient K may have information about the quality of each pixel in a 3D matrix form.

Also, the quality coefficient K may have quality information for each pixel in various ways. In an exemplary embodiment, the quality coefficient K may provide the beamformer 100 with information about a quality of each voxel by representing a higher quality with a higher index and representing a lower quality with a lower index.

In another exemplary embodiment, the quality coefficient K may have information about a quality of each voxel in a form of a dimension of the beamforming coefficient w. Specifically, a voxel determined to have a higher quality is to be beamformed into a higher resolution by increasing the dimension of the beamforming coefficient w, and a voxel determined to have a lower quality is to be beamformed into a lower resolution by decreasing the dimension of the beamforming coefficient w.

In yet another exemplary embodiment, the quality coefficient K may have information about a quality of each voxel in a form of a beamforming coefficient w to be used in beamforming. The quality determiner 200 will now be described in more detail in connection with FIGS. 5 to 7.

Figure 5:
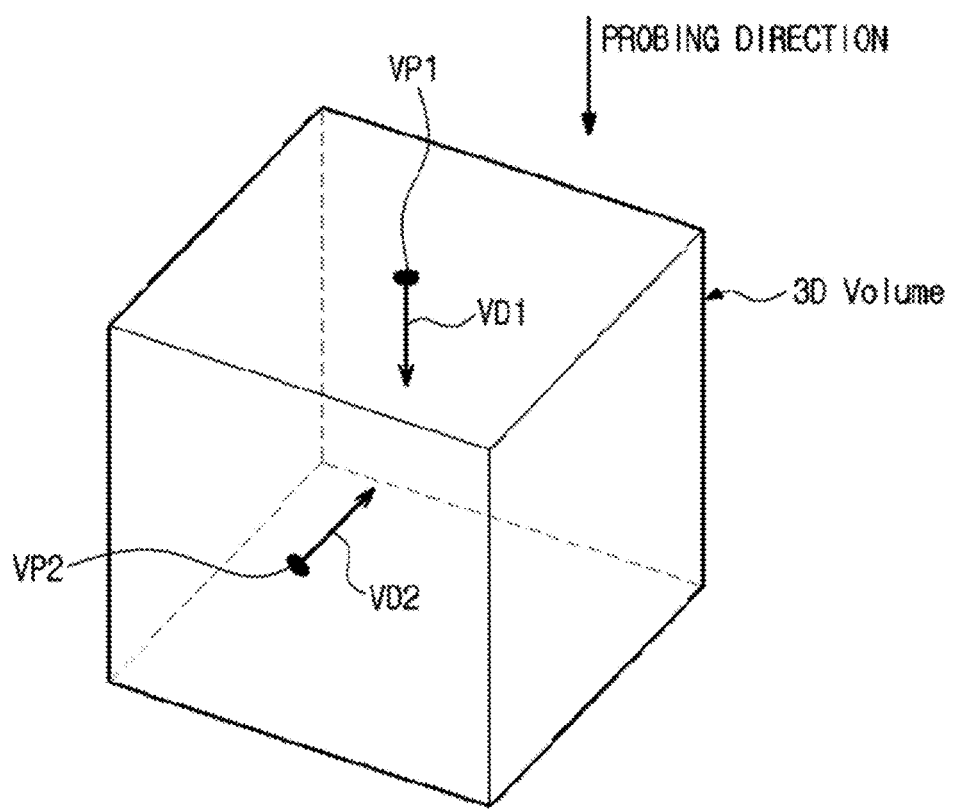
FIG. 5 is a diagram for explaining observation information of a three-dimensional (3D) volume according to an exemplary embodiment.

FIG. 5 is a diagram for explaining observation information of a 3D volume according to an exemplary embodiment.

Figure 6:
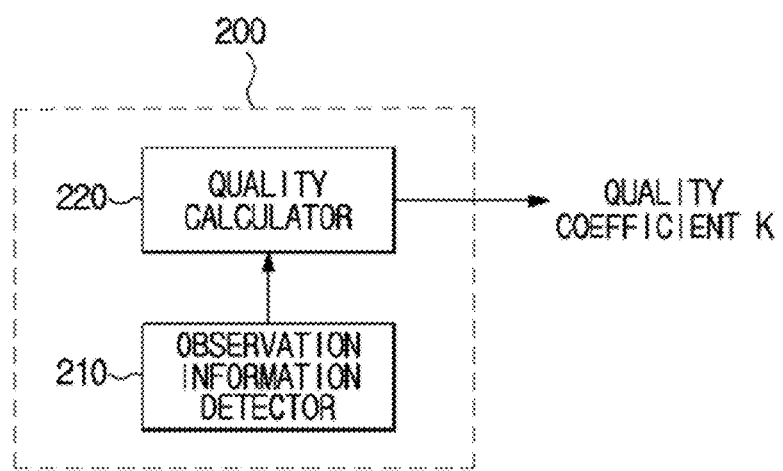
FIG. 6 is a block diagram of a quality determiner, according to an exemplary embodiment.

FIG. 6 is a block diagram of a quality determiner, according to an exemplary embodiment.

Referring to FIGS. 2, 5, and 6, the quality determiner 200 may include an observation information detector 210 and a quality calculator 220.

The observation information detector 210 detects observation information of a 3D volume. The observation information detects information regarding an area of higher interest to the user. For example, the observation information may include information about an observation center, which is a centered voxel for observation, and an observation direction, which is a direction of observation from the center of observation.

The observation information detector 210 may extract the observation information in various ways. For example, the observation information may be detected based on a probing direction of a probe and information regarding a screen to be rendered and displayed.

More specifically, the ultrasonic probe P may probe a 3D volume in a probing direction, as shown in FIG. 5. The 3D volume includes a plurality of voxels. The observation information detector 210 may detect a voxel VP1 corresponding to a center among voxels most adjacent to the ultrasonic probe P in the probing direction of the probe as the observation center, and detect a depth direction of the probe as the observation direction VD1.

The observation information may vary depending on user inputs. For example, if the user changes the observation center from VP1 to VP2 and the observation direction from VD1 to VD2, the observation information changes even if the probing direction of the probe has not been changed.

The quality calculator 220 calculates a quality of each voxel of a 3D volume based on the observation information. More specifically, the quality calculator 220 may calculate a voxel adjacent to the observation center to have a higher quality and a voxel further away from the observation center to have a lower quality. To this end, the quality determiner 200 may output a quality coefficient K of each voxel.

The quality calculator 220 may also calculate a voxel located in the observation direction to have a higher quality and a voxel located in a direction opposite to the observation direction to have a lower quality.

In addition, the quality determiner 200 may use information about the observation center and information about the observation direction, to calculate voxels adjacent to the observation center in the observation direction to have a higher quality.

FIG. 7 shows an example of a function to calculate a quality of a voxel according to an exemplary embodiment.

Referring to FIG. 7, the quality calculator 220 may calculate a quality of a voxel based only on information regarding the observation center. More specifically, the quality determiner 200 may obtain a distance between a voxel corresponding to the observation center and another voxel and calculate the quality of the voxel based on the distance, as shown in FIG. 7.

For example, the quality determiner 200 sets a voxel having a distance to the observation center vp1 shorter than a first threshold thr1 to have a highest quality value, e.g., 5, and sets lower quality values 4, 3, 2, 1 for voxels according to the distance from the voxels to the observation center vp1 based on comparison with a second threshold thr2, a third threshold thr3, and a fourth threshold thr4.

Figure 8:
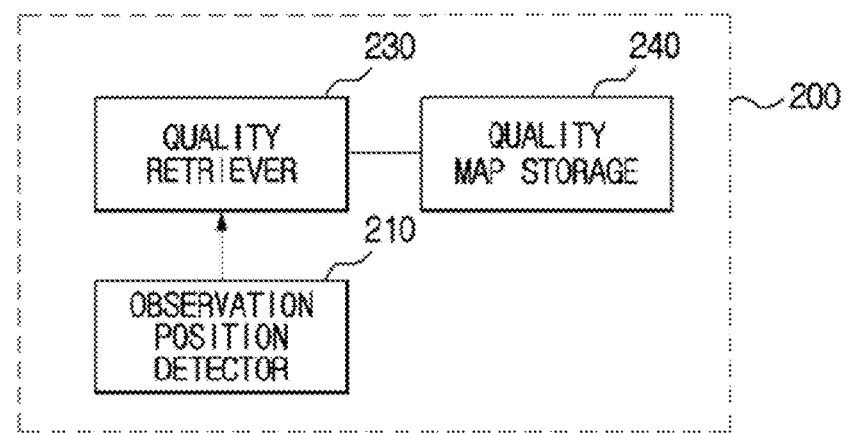
FIG. 8 is a block diagram of a quality determiner, according to an exemplary embodiment.

FIG. 8 is a block diagram of the quality determiner 200, according to an exemplary embodiment.

The quality determiner 200 includes the observation information detector 210, a quality retriever 220, and a quality map storage 240.

The quality retriever 220 may retrieve a quality map stored in the quality map storage 240 based on the observation information. The quality map has information relating to a quality of each voxel. More specifically, the quality retriever 220 retrieves the quality map based on the observation information detected by the observation information detector 210. The quality retriever 220 may retrieve a quality map corresponding to the observation information or may retrieve a quality map corresponding to observation information, which is closest to the observation information detected by the observation information detector 210.

The quality map storage 240 may store one or more quality maps. The quality map storage 240 may store quality maps prepared according to respective observation information, the quality maps being classified and stored according to the observation information.

The quality map may be, e.g., in a 3D array. A matrix of the quality map in a 3D array may store a quality of each voxel.

Figure 9:
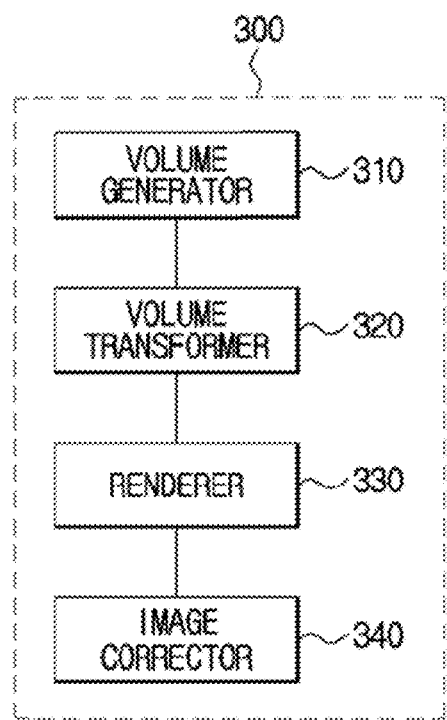
FIG. 9 is a block diagram of an image processor, according to an exemplary embodiment.

FIG. 9 is a block diagram of an image processor, according to an exemplary embodiment.

An image processor 300 generates a 3D volume by combining one or more output signals output from the beamformer 100, and renders the 3D volume to be output.

Referring to FIGS. 2 and 9, the image processor 300 may include a volume generator 310, a volume transformer 320, a renderer 330, and an image corrector 340.

The volume generator 310 may generate a 3D volume by combining one or more 2D images. A 3D volume may be generated in various ways, but for convenience of explanation, it is assumed herein that a 3D volume is generated by data interpolation.

Figure 10:
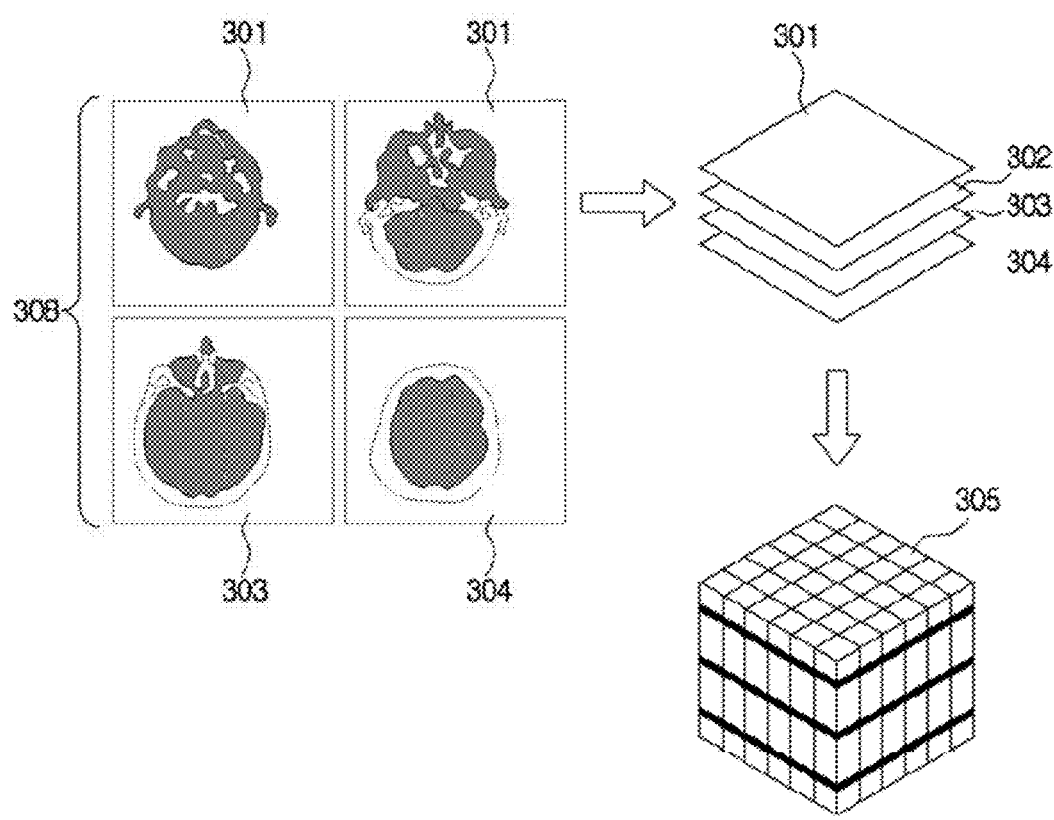
FIG. 10 illustrates a method of creating a 3D volume, according to an exemplary embodiment.

FIG. 10 illustrates a method of creating a 3D volume, according to an exemplary embodiment.

Referring to FIGS. 2, 9, and 10, a plurality of 2D cross-sectional images 308 including images 301, 302, 303, and 304 based on one or more output signals received from the beamformer 100 may be obtained. The volume generator 310 arranges the 2D cross-sectional images 308 into a 3D space, and generates a 3D volume 305 by performing data interpolation on the cross-sectional images 308.

The 3D volume may be generated in a matrix form. That is, each voxel may be represented in x, y, and z axes. Each voxel may be represented as a scalar or vector value.

More specifically, a 3D volume may be generated in a form of binary volume data if a voxel value is represented in a binary value, i.e., '0' or '1', or a 3D volume may be generated in a form of multi-quantity volume data having a measurable value, such as density and temperature.

Furthermore, based on the voxel value, values of optical components of the voxel, such as an opacity value and a color value may be obtained. The opacity value and the color value may be calculated by using an opacity transfer function that defines a relationship between the voxel value and the opacity value and a color transfer function that defines a relationship between the voxel value and the color value.

Figure 11:
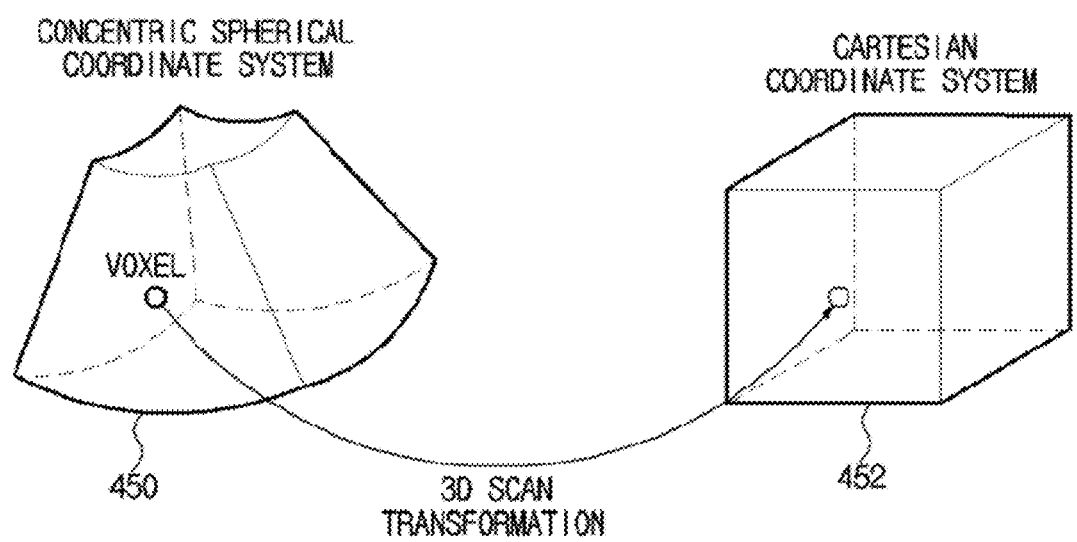
FIG. 11 illustrates volume transformation, according to an exemplary embodiment.

FIG. 11 illustrates volume transformation, according to an exemplary embodiment.

Referring to FIGS. 2, 9, and 11, the volume transformer 320 may perform scan transformation on a 3D volume. In an exemplary embodiment, if the ultrasonic probe P is in a liner shape, volume transformation may be omitted. However, if the ultrasonic probe P is in another shape, e.g., in a convex form, transformation of the volume is required into the Cartesian coordinate system.

More specifically, when a display screen uses the Cartesian coordinate system, a volume for an object needs to be in the Cartesian coordinate system to visualize a three-dimensional volume on the display screen. For example, if a volume generated from the volume generator 310 is in a concentric spherical coordinate system as shown in diagram 450 of FIG. 11, coordinate transformation is needed to visualize the volume on the display screen. Thus, a volume corrector may perform 3D scan transformation on the volume in the concentric spherical coordinate system as shown in diagram 450 of FIG. 11 to be corrected to a volume in the Cartesian coordinate system as shown in diagram 452 of FIG. 11.

Figure 12:
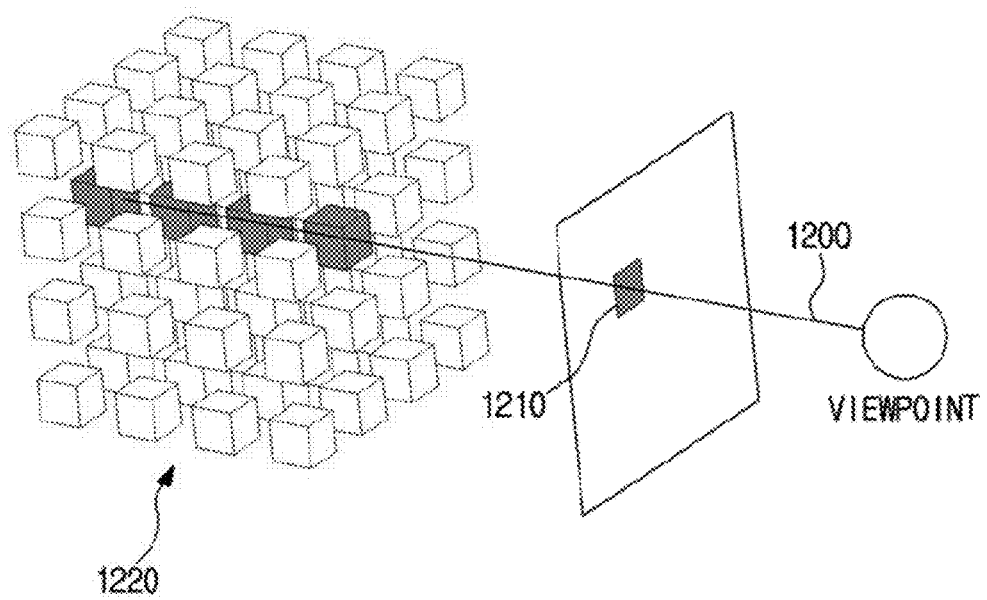
FIG. 12 illustrates volume rendering, according to an exemplary embodiment.

FIG. 12 illustrates volume rendering, according to an exemplary embodiment.

Referring to FIGS. 2, 9, and 12, the renderer 330 may perform volume rendering based on a 3D volume, to generate a projection image for an object. More specifically, the renderer 330 performs a task of visualizing a 3D volume into a 2D image, and the volume rendering largely corresponds to surface rendering and direct rendering.

The surface rendering estimates surface information from a volume based on a user-defined scalar value and spatial variation. The surface rendering visualizes the surface information by changing the surface information into a geometric element, such as e.g., a polygonal shape or a curved patch. The surface rendering may be performed, for example, by using a marching cubes algorithm.

The direct rendering is used to directly visualize a volume without intermediary stages for changing a surface into a geometric element. The direct rendering may be divided into an image-order algorithm and an object-order algorithm depending on a method for probing a volume.

The object-order algorithm is used to probe a volume in a stored order and combine each voxel with a corresponding pixel, and may use a splatting method for the object-order algorithm.

The image-order algorithm is used to determine pixel values in an image scan line order. In other words, the image-order algorithm is used to sequentially determine pixel values corresponding to a volume generated along rays transmitted from respective pixels. The image-order algorithm may be performed by using ray casting and ray tracing.

Although there are no limitations on the method for performing volume rendering in the renderer 330, it is assumed herein that the ray casting method is used by the renderer 330 for the convenience of explanation.

As shown in FIG. 12, assuming that the user stares in one direction, a straight line 1200 is created from a viewing point of the user in an eyesight direction of the user. A pixel 1210 on the straight line 1200 irradiates a virtual ray in the eyesight direction of the user. Sample points are determined at intersections of the virtual ray and a 3D volume 1220.

Once the sample points are determined, colors and opacity values for the sample points are calculated. A color and an opacity value of each sample may be calculated in an interpolation method that interpolates the color and the opacity value of the sample with colors and opacity values of voxels adjacent to the sample point.

A color and an opacity value of the pixel 1210 that irradiates the virtual ray are determined by accumulating calculated colors and opacity values of the sample points, respectively. Alternately, a respective average value or a weighted average value of the colors and opacity values of the sample points may be determined as the color and the opacity value of the pixel 1210. The determined color and opacity value becomes a pixel value of the pixel 1210 that irradiates the virtual ray.

A projection image is created by repeating the above process for all the pixels of an image.

The image corrector 340 may correct a brightness level, a contrast, a color, a size, or a direction of the projection image created by the renderer 330.

The image corrector 340 may send the corrected resulting image to the display d connected to the main unit M over a wired or wireless communication network. Accordingly, the user may view the corrected resulting image for the object displayed on the display.

Turning back to FIG. 2, the main unit M of the ultrasound imaging apparatus may include a system controller 500. The system controller 500 is configured to control operations of the ultrasound imaging apparatus including the beamformer 100, the ultrasound generation controller 510, the quality determiner 200, the image processor 300, the storage 400, the display d, etc.

Furthermore, the system controller 500 may control operations of the ultrasound imaging apparatus based on predetermined settings, and may be configured to control the ultrasound imaging apparatus by generating a predetermined control command according to the user's instruction or command input through the input unit i.

The main unit M of the ultrasound imaging apparatus may include the ultrasound generation controller 510. The ultrasound generation controller 510 generates a pulse signal according to a command from, e.g., the system controller 500 and sends the pulse signal to an ultrasound generator P21 of the ultrasonic probe P. Then, the ultrasound generator P21 generates an ultrasound from the pulse signal and transmits the ultrasound to an object. The ultrasound generation controller 510 may also generate a separate control signal for a power source 520 to apply an AC current to the ultrasound generator P21.

Figure 13:
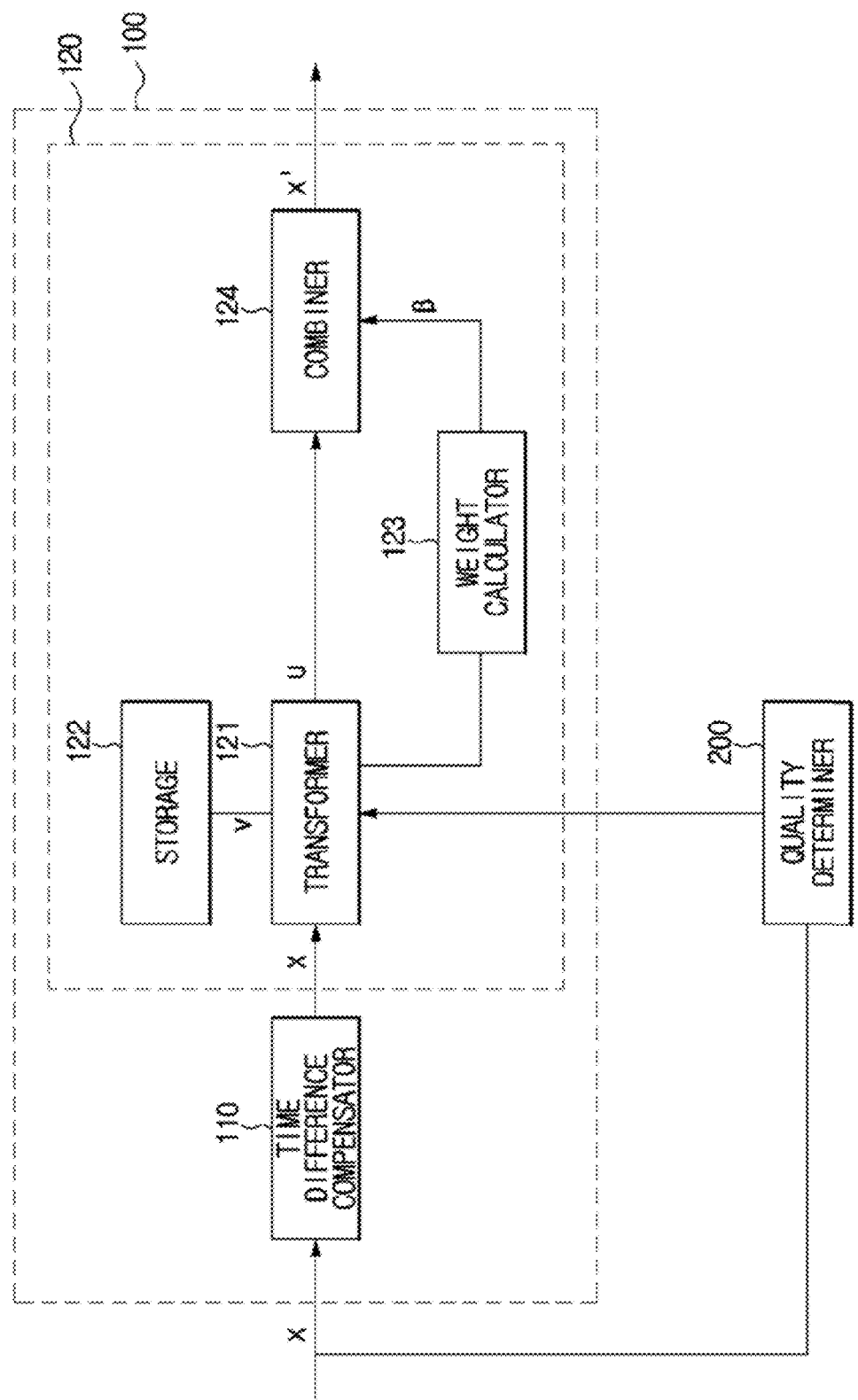
FIG. 13 is a block diagram for explaining beamforming, according to an exemplary embodiment.

FIG. 13 is a block diagram for explaining beamforming, according to an exemplary embodiment.

The beamformer 100 of the ultrasound imaging apparatus may perform beamforming based on a quality of each voxel in various ways. An example method of performing adaptive beamforming based on a quality of each voxel will now be described.

Referring to FIG. 13, the beamformer 100 includes a time difference compensator 110, a transformer 121, a transformation matrix database (or storage) 122, a weight calculator 123, and a combiner 124.

The time difference compensator 110 compensates a time difference between echo signals. A signal with a time difference compensated by the time difference compensator 110 is input to the focuser 120, and the focuser 120 focuses the input signal by applying a beamforming coefficient w.

More specifically, the transformer 121 receives a plurality of ultrasound signals x with time differences compensated by the time difference compensator 110 through a plurality of channels, and generates transformed signals u by transforming the input plurality of ultrasound signals x.

The transformer 121 may be configured to generate the transformed signals u using a predetermined transformation matrix V. In this case, the transformer 121 may operate the transformed signal u using the following equation 3.

$$u = V^H x \qquad (3)$$

where x represents an echo signal or a combined echo signal, and V represents a predetermined transformation matrix. u represents a transformed signal obtained by transforming the echo signal by using the transformation matrix V.

In an exemplary embodiment, the echo signal or combined echo signal x and the transformed signal u may be expressed in a matrix of (A×B), where A and B are positive integer numbers. When B is 1, the echo signal x and transformed signal u is expressed in a matrix of (A×1). The echo signal or combined echo signal x and the transformed signal u may be expressed in the following equations 4 and 5, respectively.

$$x = \begin{pmatrix} x_1 \\ x_2 \\ \ldots \\ x_m \end{pmatrix} \qquad (4)$$

$$u = \begin{pmatrix} u_1 \\ u_2 \\ \ldots \\ u_n \end{pmatrix} \qquad (5)$$

where m and n are positive integer numbers.

In the echo signal or combined echo signal x and the transformed signal u defined as in equations 4 and 5, respectively, the dimension of the echo signal or combined echo signal x is determined by a value of m and the dimension of the transformed signal u is determined by a value of n.

The dimension of the transformed signal u may be different per voxel depending on the quality determined by the quality determiner 200. For example, the transformed signal u corresponding to a higher quality voxel may have a dimension of five, and the transformed signal u corresponding to a lower quality voxel may have a dimension of one. Such quality-based differential determination of the dimension of the transformed signal u may reduce an amount of calculations that may occur in beamforming.

Each element of a matrix for the echo signal x of equation 4, e.g., $x_m$, may refer to an echo signal input from the m-th channel or a combined echo signal on the m-th channel. Similarly, each element of the transformed signal u of equation 5, e.g., $u_n$, refers to a transformed signal on an n-th channel, resulting from transformation of an echo signal on the $n^{th}$ channel. Of course, elements of the echo signal x and the transformed signal u (i.e., $x_1$ to $x_m$, and $u_1$ to $u_n$) may also be each defined in a predetermined matrix, e.g., (1×a) where a is a positive integer number.

The transformer 121 may call a transformation matrix V from the transformation matrix database 122, and use the transformation matrix V to generate the transformed signal u. In this case, the transformer 121 may select a transformation matrix V corresponding to a quality of a voxel from the transformation matrix database 122, and generate the transformed signal u for the ultrasound signal x based on the selected transformation matrix V.

In an exemplary embodiment, the transformation matrix database 122 may store at least one transformation matrix V corresponding to a quality of a voxel. In this case, the at least one transformation matrix V stored in the transformation matrix database 122 may be pre-calculated based on various forms of ultrasound signal x that may be obtained empirically or theoretically. For example, the at least one transformation matrix V may be calculated using a number of ultrasound signals x obtained through transmission of an ultrasound onto a separate specimen in advance.

More specifically, transformation matrices V included in the transformation matrix database 122 may include a basis vector or a combination of a plurality of basis vectors obtained based on a predetermined beamforming coefficient w, which are calculated in advance. The pre-calculated beamforming coefficient w may be calculated using various forms of ultrasound signals x that may be obtained empirically or theoretically.

The beamforming coefficient w may be obtained by applying a minimum variance algorithm to ultrasound signals x on multiple channels. The basis vectors obtained based on the beamforming coefficient w may be obtained by performing a principal component analysis on the beamforming coefficient w. The plurality of basis vectors that form the transformation matrix V may be orthogonal vectors substantially perpendicular to one another, or more specifically, eigenvectors or Furrier basis vectors.

In another exemplary embodiment, the transformation matrix database 122 may store at least one basis vectors for forming the transformation matrix V. In this case, the transformer 121 may call at least one basis vector from the transformation matrix database 122 and use the at least one basis vector to generate a transformation matrix V for the ultrasound signal x.

The number of the basis vectors that form the transformation matrix V may depend on the quality of each voxel. For example, a voxel having a higher quality uses a transformation matrix V with a greater number of basis vectors and a voxel having a lower quality uses a transformation matrix V with a smaller number of basis vectors.

In an exemplary embodiment, the weight calculator 123 receives the transformed signal u from the transformer 121 and calculates at least one weight to be used by the combiner 124 based on the transformed signal u. In another exemplary embodiment, the weight calculator 123 directly receives the ultrasound signal x with a time difference compensated by the time difference compensator 110 and calculates at least one weight based on the ultrasound signal x.

The weight calculator 123 calculates a signal weight $\beta$. More specifically, the weight calculator 123 calculates the signal weight $\beta$ to be applied to the transformed signal u output from the transformer 121. In this case, the weight calculator 123 uses the ultrasound signal x and/or the transformation matrix V to calculate the signal weight $\beta$ for the transformed signal u.

More specifically, the weight calculator 123 may calculate the signal weight $\beta$ according to the following equation 6:

$$\beta = \frac{R^{-1}a}{a^H R^{-1} a} \quad (6)$$

$\beta$ represents a signal weight. R represents a covariance for each echo signal x input from one of multiple channels, and a represents a steering vector.

The covariance R may be expressed as in the following equation 7:

$$R = E(XX^T) \quad (7)$$

X represents a matrix for the echo signal x, e.g., a matrix of (1×m).

In an exemplary embodiment, the covariance R may be a transformed covariance R1 resulting from transformation of the covariance for the echo signal x, as calculated in equation 7. That is, the covariance R may be a transformed covariance for the echo signal x. In this case, to perform transformation of the covariance R, the transformation matrix V retrieved from the transformation matrix database 122 may be used. The transformed covariance R1 may be expressed as in the following equation 8:

$$R_1 = V^H R V \quad (8)$$

The steering vector a is to control a phase of a signal. In an exemplary embodiment, the steering vector a of equation 6 may also be a transformed steering vector v1. In this case, to perform transformation of the steering vector a, the same transformation matrix V as that used for transformation of the covariance R may be used. Specifically, the transformed steering vector v1 may be calculated by the following equation 9:

$$v_1 = V^H a \quad (9)$$

Substituting the covariance R and the steering vector a with the transformed covariance R1 and the transformed steering vector v1, respectively, in equation 6, the signal weight $\beta$ may be calculated in the following equation 10.

$$\beta = \frac{R_1^{-1} v_1}{v_1^H R_1^{-1} v_1} \quad (10)$$

The signal weight $\beta$ is calculated according to the equation 6 or 10. As represented in equation 6 or 10, in various exemplary embodiments, the signal weight $\beta$ may depend on the input echo signal x or the transformed steering vector v1, which depends on the transformation matrix V, as shown in equation 9. Since the transformation matrix V may be predefined and selected according to the echo signal x, the signal weight $\beta$ may usually depend on the echo signal x.

The signal weight $\beta$ may be in a form of a column vector, and if the transformation matrix V is expressed in an (M×N) matrix, the signal weight $\beta$ is in an (N×1) matrix, i.e., an (N×1) column vector.

Accordingly, as described above, complexity of calculation of the signal weight $\beta$ may depend on a dimension of the transformation matrix V. In other words, the transformation matrix V for a voxel with a higher quality may be represented in a higher dimensional matrix and thus need a greater amount of calculations for obtaining the signal weight $\beta$, while the transformation matrix V for a voxel with a lower quality is represented in a lower dimensional matrix, thus calculating the signal weight $\beta$ with less calculations.

The combiner 124 may generate a beamformed ultrasound signal x' by combining the time difference-compensated ultrasound signals x. Specifically, the combiner 124 may be configured to combine the ultrasound signals as illustrated in FIG. 13.

For example, as shown in FIG. 13, a plurality of ultrasound signals on their respective channels are combined first to generate a combined ultrasound signal of the plurality of channels. Then, the combined ultrasound signal of the plurality of channels is processed to generate the beamformed ultrasound signal x'. In processing the combined ultrasound signal of the plurality of channels, the combiner 124 uses a predetermined weight. Specifically, the combiner 124 may generate the beamformed ultrasound signal x' by weighted summation of the combined ultrasound signal of the plurality of channels and the predetermined weight. In this regard, the weight may be an ultrasound signal weight β sent from the weight calculator 123.

The combiner 124 produces the signal x' based on the transformed signal u generated and output from the transformer 121 and the signal weight β calculated by the weight calculator 123. In this case, the combiner 124 may generate the signal x' by combining the transformed signal u and the signal weight β, e.g., by performing weighted summation of the transformed signal u and the signal weight β. Consequently, the beamformer 100 may generate and output the signal x' resulting from beamforming on an echo signal x.

In an exemplary embodiment, the combiner 124 may be configured to calculate the signal x' based on the transformed signal u and the signal weight β according to the following equation 11.

$$z = \beta^H u \quad (11)$$

where z is a resulting signal, β is a signal weight calculated from the weight calculator 123, and u is a transformed signal resulting from transformation of the echo signal x.

That is, equation 11 may be rewritten into the following equation 12:

$$\begin{aligned} x' &= \beta^H u \\ &= \beta^H V^H x \\ &= (V\beta)^H x \end{aligned} \quad (12)$$

If the beamforming coefficient w is defined as in the following equation 13, equation 11 may be expressed as in the following equation 14:

$$w = V\beta \quad (13)$$

$$x' = \beta^H u = w^H x \quad (14)$$

Examining equation 14, the right term is equal to equation 11. That is, equation 12 may be expressed as in equation 14.

In other words, if the beamforming coefficient w is defined as in equation 13, the beamformed ultrasound signal x' output from the combiner 124 according to equation 12 may be equal to the weighted summation of the ultrasound signal x and a predetermined weight, i.e., the beamforming weight w.

Figure 14:
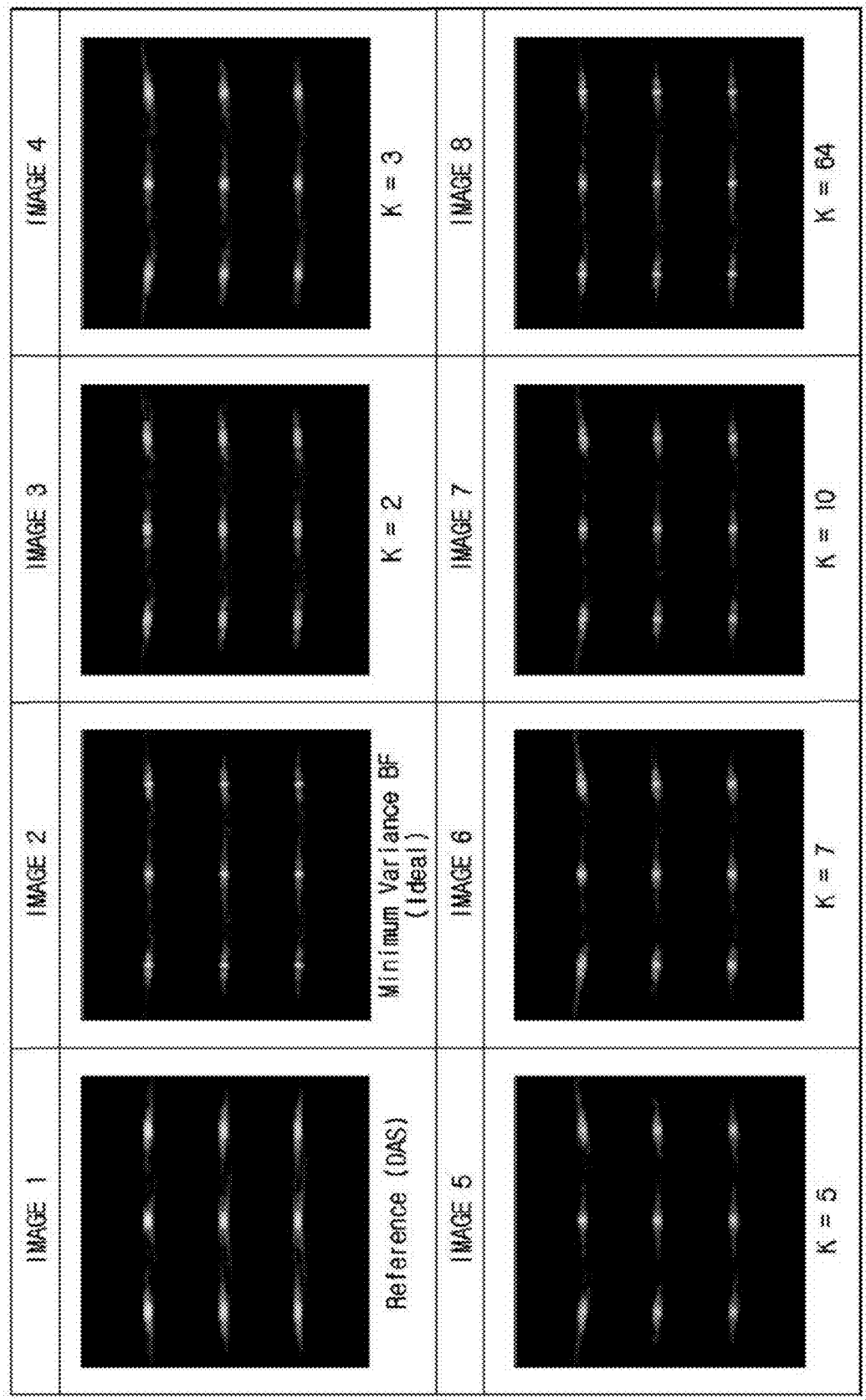
FIG. 14 illustrates quality-based ultrasonic images according to an exemplary embodiment.
Figure 15:
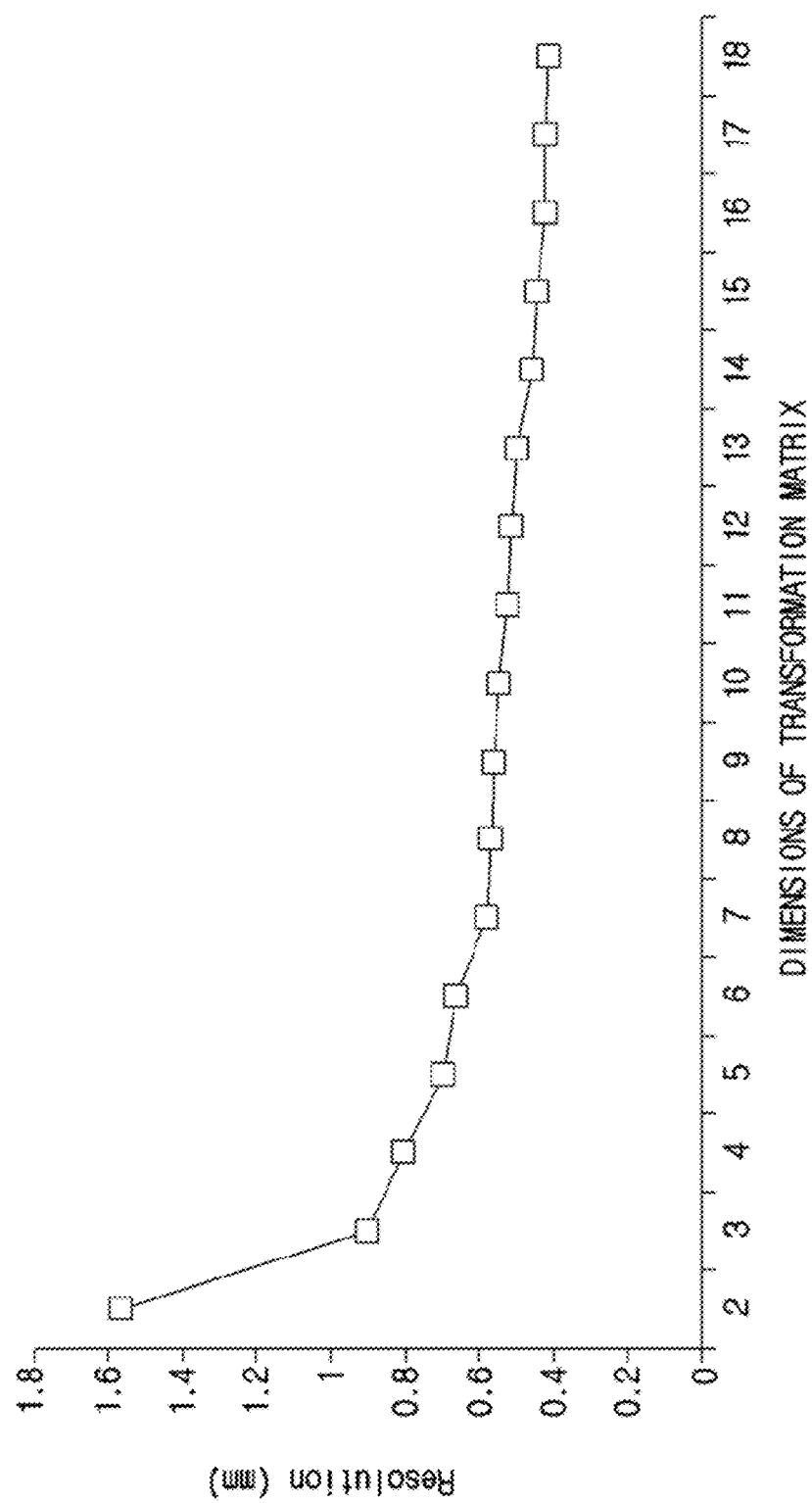
FIG. 15 illustrates a graph describing resolutions of quality-based ultrasonic images.

FIG. 14 illustrates quality-based ultrasonic images according to an exemplary embodiment. FIG. 14 shows an ultrasonic image of B mode or brightness mode, and the vertical axis of FIG. 14 refers to a depth of a target part. FIG. 15 illustrates a graph describing resolutions of quality-based ultrasonic images with respect to dimensions of a transformation matrix, according to an exemplary embodiment.

As shown in FIG. 14, resolutions of an ultrasonic image 2, an ultrasonic image 3, an ultrasonic image 4, an ultrasonic image 5, an ultrasonic image 6, an ultrasonic image 7, and an ultrasonic image 8 resulting from adaptive beamforming that uses a minimum variance algorithm is higher than that of ultrasonic image 1 resulting from fixed beamforming (e.g., delay-and-sum (DAS) beamforming). As shown in FIG. 14, the ultrasonic images 3 to 8 are obtained by using a quality coefficient K of each voxel determined by the quality determiner 200. Specifically, the ultrasonic image 3 is beamformed by using a quality coefficient k of 2, the ultrasonic image 4 is beamformed by using a quality coefficient k of 3, the ultrasonic image 5 is beamformed by using a quality coefficient k of 5, the ultrasonic image 6 is beamformed by using a quality coefficient k of 7, the ultrasonic image 7 is beamformed by using a quality coefficient k of 10, and the ultrasonic image 8 is beamformed by using a quality coefficient k of 64. Although the minimum variance algorithm has higher burden of calculations, performing beamforming based on pixel quality of each volume as described above may increase beamforming performance.

As compared with the ultrasonic image 2 that has been ideally beamformed according to the minimum variance algorithm, the ultrasonic images 5 to 8 may obtain higher resolution with less burden of calculations.

FIG. 15 illustrates a graph describing resolutions of quality-based ultrasonic images according to an exemplary embodiment. A horizontal axis of the graph in FIG. 15 represents dimensions of the transformation matrix and a vertical axis thereof represents resolutions of the resultant quality-based ultrasonic images.

Referring to FIG. 15, when the transformation matrix has a dimension of 5 or more, it is seen that an increase in dimensions does not result in a noticeable change in resolution. Accordingly, a quality of each voxel may be adjusted by changing the dimension of the transformation matrix from 1 to 5.

For example, a voxel with the highest quality may be beamformed with five-dimensional transformation matrix, and a voxel with the lowest quality may be beamformed with one-dimensional transformation matrix.

Figure 16:
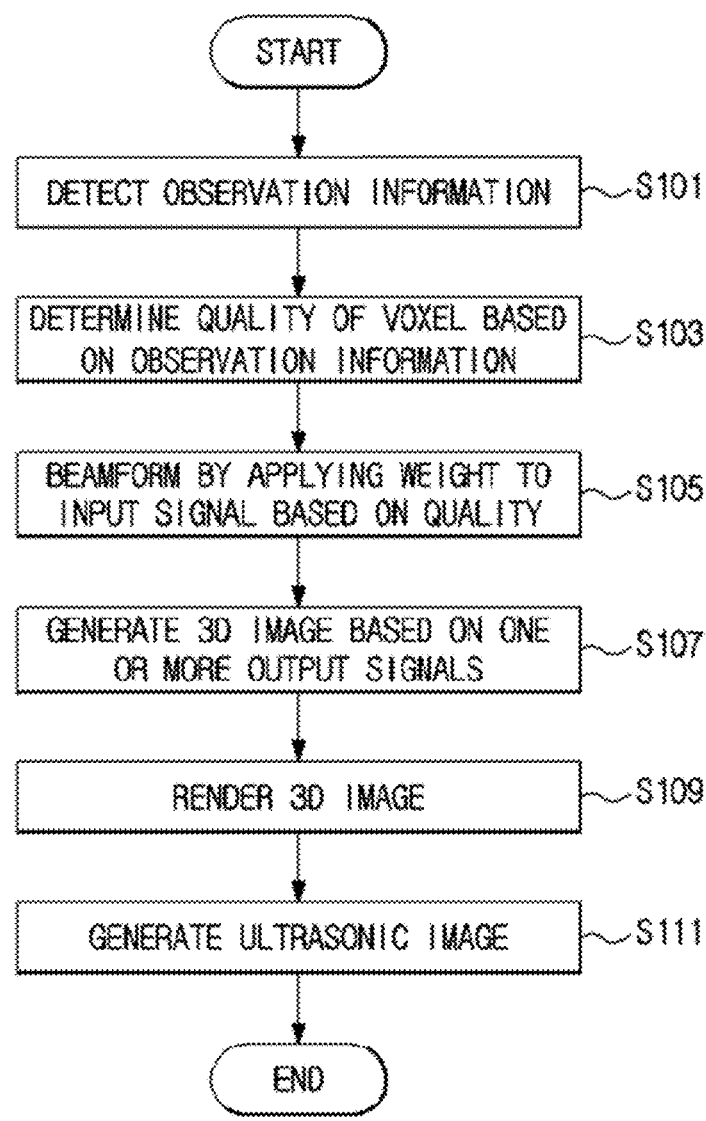
FIG. 16 is a flowchart illustrating a method for controlling an ultrasound imaging apparatus, according to an exemplary embodiment.

FIG. 16 is a flowchart illustrating a method for controlling an ultrasound imaging apparatus, according to an exemplary embodiment.

Referring to FIG. 16, the ultrasound imaging apparatus detects observation information in operation S101. The observation information may be detected by considering when to render a 3D volume probed by the ultrasonic probe P. More specifically, the observation information may include an observation center and an observation direction for the 3D volume, which may be detected based on various criteria, including a user input, a probing direction of the probe P, etc.

The ultrasound imaging apparatus determines a quality of a voxel according to the detected observation information, in operation S103. In an exemplary embodiment, the quality of a voxel may be determined according to a preset function. The preset function may determine the quality of the voxel based on a distance between the observation center and each voxel. In addition, the preset function may also consider the observation direction in determining the quality of the voxel.

In another exemplary embodiment, the quality of each voxel may be determined by selecting at least one of pre-stored quality maps. To this end, the ultrasound imaging apparatus may include a plurality of quality maps including qualities of respective voxels corresponding to the observation information. When the pre-stored quality map and the observation information do not exactly match, a quality map corresponding to the closest observation information may be selected.

The ultrasound imaging apparatus performs beamforming by applying a weight to an echo signal based on the determined quality, in operation S105.

The ultrasound imaging apparatus generate a 3D image based on one or more output signals, in operation S107.

For example, echo signals of multiple channels may be focused by compensating time differences among signals on respective channels, upon reception of the multiple echo signals, and stressing or attenuating respective echo signals of the channels with predetermined weights.

Each voxel may require different burden of calculations in beamforming, depending on the determined quality of the voxel. Specifically, a voxel with a higher quality may be beamformed with a relatively great amount of calculations, and a voxel with a lower quality may be beamformed with less calculation but at faster speed.

The ultrasound imaging apparatus generate a 3D image based on one or more output signals. More specifically, one or more output signals, which have been beamformed, are collected, and a plurality of 2D cross-sectional images are obtained from the collected output signals. Then, a 3D volume is generated by arranging the obtained 2D cross-sectional images in order. Gaps among the 2D cross-sectional images may be processed with data compensation.

When needed, the generated 3D volume may be processed with scan transformation and be transformed into the Cartesian coordinate system.

The ultrasound imaging apparatus renders a 3D image, in operation S109. In this regard, a projection image is generated by performing volume rendering based on the 3D volume. When needed, the projection image may be post-processed.

The ultrasound imaging apparatus outputs an ultrasonic image, in operation S111. If the observation information changes due to, e.g., a user input after the ultrasonic image is output, the process may return to operation S101 to perform the above operations with the changed observation information.

Figure 17:
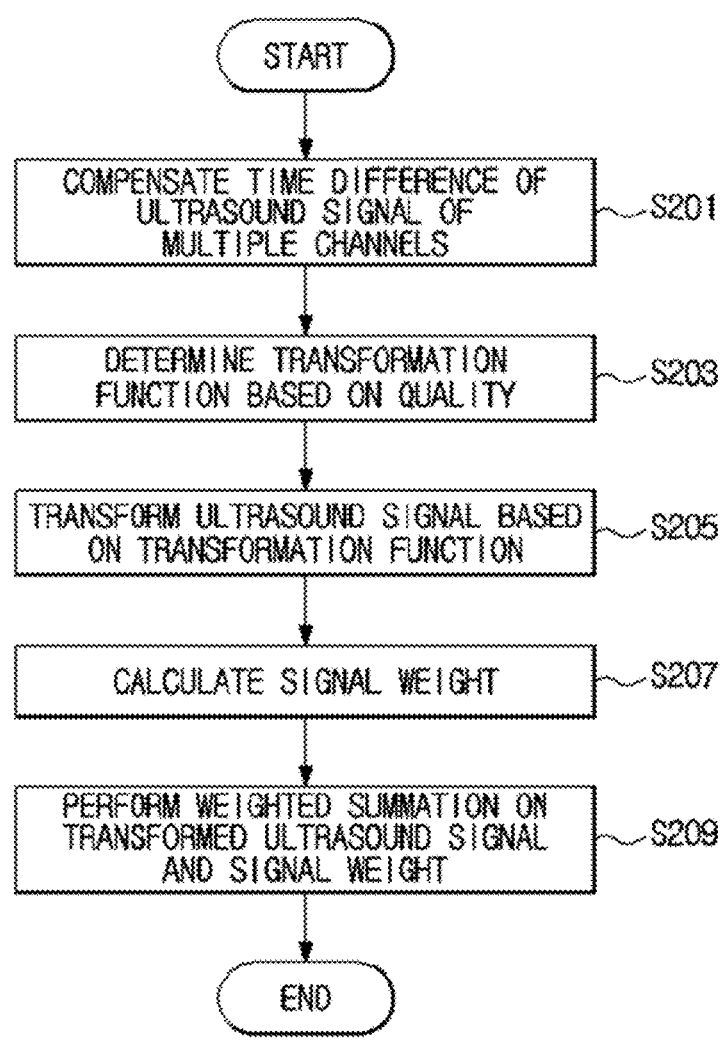
FIG. 17 is a flowchart illustrating a method for quality-based beamforming of an ultrasound imaging apparatus, according to an exemplary embodiment.

FIG. 17 is a flowchart illustrating a method for quality-based beamforming of an ultrasound imaging apparatus, according to an exemplary embodiment.

The ultrasound imaging apparatus may differentially perform beamforming on a quality basis. An exemplary embodiment of adaptive beamforming will now be described.

Referring to FIG. 17, the ultrasound imaging apparatus may compensate time differences among ultrasound signals of a plurality of channels, in operation S201. The ultrasound imaging apparatus may compensate time differences among multiple echo signals.

The ultrasound imaging apparatus may determine a transformation matrix on a quality basis, in operation S203. The transformation matrix changes echo signals to transformed signals. At this time, dimensions of the transformed signals are determined according to the transformation matrix. Thus, the transformation matrix may be different depending on voxels to be beamformed.

In an exemplary embodiment, the transformation matrixes are formed to include one or more basis vectors. The basis vector may be generated in various ways. The basis vector may be obtained through a principal component analysis for a beamforming coefficient w. The beamforming coefficient w used for the principal component analysis may be obtained empirically or from statistical data. For example, the beamforming coefficient w may be calculated by a minimum variance algorithm.

In other words, the number of basis vectors to be used to form the transformation matrix may depend on the quality of a voxel on which beamforming is performed. As such, the less the number of basis vectors is, the lower the resolution is, and the greater the number of basis vectors is, the higher the resolution is but the greater the burden of calculation is.

In another exemplary embodiment, a transformation matrix may be selected from among multiple transformation matrices corresponding to different qualities.

The ultrasound imaging apparatus may transform an ultrasound signal according to the transformation matrix, in operation S205. A transformed signal may be generated using the transformation matrix determined according to a quality of a voxel. The dimension of the transformed signal is determined according to the transformation matrix. For example, in beamforming a voxel with a higher quality, the transformed signal has a higher dimension, and in beamforming a voxel with a lower quality, the transformed signal has a lower dimension.

The ultrasound imaging apparatus may calculate a signal weight, in operation S207. The signal weight may be calculated based on the transformation matrix or an echo signal. The signal weight may be a weight to be summed with the transformed signal. The signal weight may also be generated based on the transformation matrix. Thus, if the transformation matrix has a low dimension, the amount of calculations is reduced and thus fast calculation is achieved.

The ultrasound imaging apparatus may perform weight summation on the transformed signal and the signal weight, in operation S209. The weight summation on the transformed signal and the signal weight is equal to the beamforming coefficient w.

Although it is described that operation S205 is followed by operation S207, the operations S205 and S207 may be performed simultaneously.

The foregoing exemplary embodiments and advantages are merely exemplary and are not to be construed as limiting. The present teaching can be readily applied to other types of apparatuses. The description of the exemplary embodiments is intended to be illustrative, and not to limit the scope of the claims, and many alternatives, modifications, and variations will be apparent to those skilled in the art.

What is claimed is:

1. An ultrasound imaging apparatus comprising:
an ultrasonic probe configured to transmit an ultrasound to an object, receive an echo signal reflected from the object, and output the echo signal;
a quality determiner, implemented by at least one processor, configured to receive the echo signal and determine quality of voxels of a three-dimensional (3D) volume of the object to be rendered based on a distance between each of the voxels and an observation center of the 3D volume; and
a beamformer, implemented by the at least one processor, configured to control beamforming differently on the echo signal based on the quality of the voxels to generate an output signal,
wherein the quality determiner is configured to determine a first voxel having a first distance to the observation center shorter than a first threshold to have highest quality, determine a second voxel having a second distance to the observation center equal to or longer than a second threshold to have a lowest quality,
wherein the beamformer is configured to perform the beamforming such that the first voxel having the highest quality has a highest resolution and the second voxel having the lowest quality has a lowest resolution, and wherein the quality determiner is configured to determine a voxel corresponding to a center among voxels most adjacent to the ultrasonic probe in a probing direction of the ultrasonic probe as the observation center.

2. The ultrasound imaging apparatus of claim 1, wherein the quality determiner is configured to extract at least one of the observation center and an observation direction of the 3D volume.

3. The ultrasound imaging apparatus of claim 2, wherein the quality determiner is configured to extract the observation center and the observation direction of the 3D volume, and determine a voxel adjacent to the observation center in the observation direction to have higher quality.

4. The ultrasound imaging apparatus of claim 1, wherein the quality determiner is configured to:
retrieve a quality map that corresponds to the distance from a quality map storage to determine the quality of the voxels, from among one or more quality maps that have information about the quality of the voxels of the 3D volume corresponding to the distance between each of the voxels and the observation center.

5. The ultrasound imaging apparatus of claim 1, wherein the beamformer is configured to perform beamforming with higher quality on voxels having higher quality.

6. The ultrasound imaging apparatus of claim 1, wherein the beamformer is configured to:
generate a transformed signal from the echo signal by using a transformation matrix corresponding to the distance between the observation center and each of voxels;
obtain a signal weight to be applied to the transformed signal; and
generate the output signal by using the transformed signal and the obtained signal weight.

7. The ultrasound imaging apparatus of claim 6, wherein the beamformer is configured to reduce a dimension of the echo signal by using the transformation matrix according to the quality of the voxel.

8. The ultrasound imaging apparatus of claim 6, wherein the beamformer is configured to store basis vectors of the transformation matrix in a storage, and
wherein a number of the basis vectors is determined based on the quality of the voxel.

9. The ultrasound imaging apparatus of claim 6, wherein the transformation matrix comprises a combination of basis vectors obtained through a principal component analysis on the quality of the voxel.

10. The ultrasound imaging apparatus of claim 1, further comprising:
an image processor configured to generate a 3D volume based on one or more output signals, output by the beamformer, and render the 3D volume into a two-dimensional (2D) plane.

11. A method for controlling an ultrasound imaging apparatus, the method comprising:
obtaining a distance between an observation center and each of voxels of a three-dimensional (3D) volume of an object to be rendered; and
determining quality of the voxels of the 3D volume based on the distance; and
performing beamforming differently on the voxels based on the determined quality,
wherein the determining quality of the voxels of the 3D volume based on the distance comprises:
determining a voxel corresponding to a center among voxels most adjacent to an ultrasonic probe in a probing direction of the ultrasonic probe as the observation center,
determining a first voxel having a first distance to the observation center shorter than a first threshold to have highest quality, and
determining a second voxel having a second distance to the observation center equal to or longer than a second threshold to have lowest quality, and
wherein the performing beamforming differently on the voxels based on the determined quality comprises performing beamforming such that the first voxel having the highest quality has a highest resolution and the second voxel having the lowest quality has a lowest resolution.

12. The method of claim 11, further comprises obtaining information about at least one of the observation center and an observation direction of the 3D volume.

13. The method of claim 11, wherein the determining the quality of the voxels comprises:
retrieving a quality map having information about the quality of the voxels of the 3D volume corresponding to the distance between the observation center and each of voxels; and
determining the quality of the voxels according to the retrieved quality map.

14. The method of claim 11, wherein the performing beamforming comprises:
transforming an echo signal to a transformed signal by using a transformation matrix corresponding to the determined quality of a respective voxel;
obtaining a signal weight to be applied to the transformed signal; and
generating an output signal using the transformed signal and the signal weight.

15. The method of claim 14, wherein the transformation matrix comprises one or more basis vectors generated through a principal component analysis, and
wherein a number of the one or more basis vectors is determined based on the determined quality of the respective voxel.

16. The method of claim 11, further comprising:
generating a 3D volume based on one or more output signals resulting from beamforming; and
rendering the 3D volume image into a two-dimensional (2D) plane.

* * * * *